United States Patent
Kennedy (10) Patent No.: US 7,205,546 B1
(45) Date of Patent: Apr. 17, 2007

(54) SPHERICAL PET MAMMOGRAPHY SCANNER

(76) Inventor: Stephen W. Kennedy, 10173 Mosaic Way, Elk Grove, CA (US) 95758

( * ) Notice: Subject to any disclaimer, the term of this patent is extended or adjusted under 35 U.S.C. 154(b) by 133 days.

(21) Appl. No.: 10/938,803

(22) Filed: Sep. 10, 2004

Related U.S. Application Data (60) Provisional application No. 60/502,315, filed on Sep. 12, 2003.

(51) Int. Cl.
*G01T 1/161* (2006.01)
(52) U.S. Cl. ................................ 250/363.02
(58) Field of Classification Search ........... 250/363.03, 250/363.02
See application file for complete search history.

(56) References Cited

U.S. PATENT DOCUMENTS

| | | | | |
|---|---|---|---|---|
| 4,559,597 A | * | 12/1985 | Mullani | ........... 600/407 |
| 5,451,789 A | * | 9/1995 | Wong et al. | ........... 250/363.03 |
| 2003/0197127 A1 | * | 10/2003 | Wainer et al. | ......... 250/363.02 |
| 2003/0205676 A1 | * | 11/2003 | Nelson et al. | ......... 250/370.09 |
| 2004/0129886 A1 | * | 7/2004 | Lecoq | ................... 250/363.03 |

* cited by examiner

*Primary Examiner*—David Porta
*Assistant Examiner*—Marcus Taningco
(74) *Attorney, Agent, or Firm*—John P. O'Banion (57) ABSTRACT

A PET mammography detector having an ellipsoidal detection surface. The ellipsoidal detection surface comprises at least one scintillation element, and is configured such that a larger portion of gamma ray emissions strike normal or near normal to the detection surface than in rectangular or cylindrical detection surfaces. The detection surface is preferably spherical, but may also be an oblate or prolate spheroid. The detector may also include a positioning ring and table to allow imaging of the patient's breast while the breast hangs freely and uncompressed inside the detector.

28 Claims, 5 Drawing Sheets

SPHERICAL PET MAMMOGRAPHY SCANNER

CROSS-REFERENCE TO RELATED APPLICATIONS

This application claims priority from U.S. provisional application Ser. No. 60/502,315 filed on Sep. 12, 2003, incorporated herein by reference in its entirety.

STATEMENT REGARDING FEDERALLY SPONSORED RESEARCH OR DEVELOPMENT

Not Applicable

INCORPORATION-BY-REFERENCE OF MATERIAL SUBMITTED ON A COMPACT DISC

Not Applicable

NOTICE OF MATERIAL SUBJECT TO COPYRIGHT PROTECTION

A portion of the material in this patent document is subject to copyright protection under the copyright laws of the United States and of other countries. The owner of the copyright rights has no objection to the facsimile reproduction by anyone of the patent document or the patent disclosure, as it appears in the United States Patent and Trademark Office publicly available file or records, but otherwise reserves all copyright rights whatsoever. The copyright owner does not hereby waive any of its rights to have this patent document maintained in secrecy, including without limitation its rights pursuant to 37 C.F.R. § 1.14.

BACKGROUND OF THE INVENTION

Breast cancer is the most common malignant tumor in women in the United States and is second only to lung cancer as a cause of cancer death in women. Despite campaigns to educate women on regular breast self-examination and the widespread use of screening mammography, many breast cancers are not discovered until after they have undergone distant metastasis and the prognosis is poor. Mammography not only has a high false negative rate, which allows many early tumors to go undetected, but also has a high false positive rate resulting in many unnecessary biopsies with their attendant costs and morbidities.

One significant advancement in locating malignant tumors in the body has been the development of PET (Positron Emission Tomography) scanners. PET is a nuclear medicine technology that uses radioisotopes to allow the noninvasive diagnostic imaging of metabolic processes in various organ systems of the human body. Images are obtained from positron-emitting radioactive tracer substances (radiopharmaceuticals) that are usually administered intravenously to the patient. Where as computed tomography (CT) and magnetic resonance imaging (MRI) provide information about anatomic structure, PET can image and quantify biochemical and/or physiological function. This information is potentially valuable because functional changes caused by disease are frequently detectable before any structural abnormalities become evident.

PET scanners currently in clinical use are cylindrical in shape and the patient is passed through the bore of the cylinder during the imaging process. While cylinders may have advantages in terms of simplicity of construction and compact size, they have serious drawbacks as imaging devices for Positron Emission Tomography. Many of the corrections that complicate image reconstruction in PET have their roots in the cylindrical shape of the detector. Most efforts to improve contrast and resolution of cylindrical PET scanners have focused on improving crystal sensitivity and detection electronics as opposed to changing detector geometry.

Breast cancer screening with PET could have the potential to detect malignant tumors much earlier in their natural history than current screening imaging techniques, improving the chances for curative therapy. To justify the increased cost and time required to do screening PET studies for breast cancer, the PET detection system needs to be optimized so the sensitivity and specificity are so clearly superior to conventional imaging techniques that it will be accepted both on clinical and economic grounds by patients and third party payers.

To date, clinical use of PET in breast cancer consists of whole body studies using conventional cylindrical detectors for tumor staging. Even with less than ideal detector geometry, PET has shown greater sensitivity and specificity than any other imaging modality in detecting metastatic disease.

Figure 1:
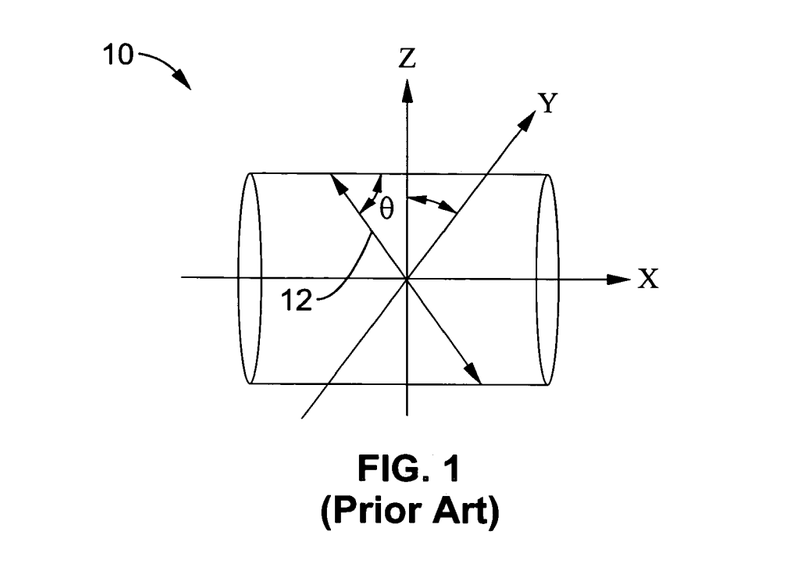
FIG. 1 illustrates a prior art cylindrical PET detector 10 typically employed for whole-body scanning.

FIG. 1 illustrates a cylindrical PET detector 10 typically employed for whole-body scanning. Cylindrical detectors imaging a mono-energetic point source will record different energy levels for photons since only the slice at the location of the source will detect photons normal to its surface. All other photons 12 will strike the detector surface at an angle θ. In addition, in a cylindrical configuration, there are no counts from the accessible front side of the breast. This reduces sensitivity, contrast and resolution and may small lesions near the areola and nipple.

Dedicated PET mammography prototype devices have been built and are currently being used in research settings. However, these devices use planar scintillation detectors to image the compressed breast during conventional mammography and are therefore subject to the limitations of planar imaging, as they lack the sensitivity to reliably detect the smallest and hence most curable malignancies.

Accordingly, an object of the present invention is to provide an improved non-planar and non-cylindrical PET detection system that provides for higher resolution and contrast in tumor detection so that a malignant tumor can be located at earlier stages of growth, and smaller tumor sizes can be identified.

Another object of the present invention is to provide a mammography PET detection system that improves the detection of breast cancer growths and the capacity to distinguish between malignant and benign breast tumors. At least some of these objectives will be met in the inventions described hereinafter.

BRIEF SUMMARY OF THE INVENTION

The present invention generally comprises a PET mammography scanner having an ellipsoidal, or near spherical geometry. Compared to conventional scanners with planar or rectangular geometries, the spherical geometry of the present invention provides for higher resolution and contrast. Beneficially, therefore, a tumor can be located at earlier stages of growth, and smaller tumor sizes can be identified. Current technology can sense tumors on the order of 1 cm in size, which is approximately 30 doublings in growth since the malignant transformation of the first tumor cell. The present invention, on the other hand, is intended to locate tumors that are about 3 orders of magnitude smaller.

According to an aspect of the invention, an apparatus is disclosed for generating a PET image of an area of interest on a patient. The apparatus generally comprises a detector having an ellipsoidal surface, wherein the detector is configured such that the ellipsoidal surface encloses at least a portion of the area of interest. A scintillation element is disposed on the ellipsoidal surface, and the scintillation element is configured to generate light in response to gamma rays striking the ellipsoidal surface. Ideally, the ellipsoidal detector surface is substantially spherical, but may take a number of configurations, such as an oblate or prolate spheroid.

In a preferred embodiment, an array of scintillation elements is disposed on the ellipsoidal surface. One or more photomultipliers may be coupled to one or more of the scintillation elements, the photomultiplier configured to convert the light emitted from the scintillation element into electronic signals. Typically, a computer is coupled to the photomultiplier to process the signals. The scintillation element generally comprises a crystal made of BOO, LSO or the like.

In a preferred embodiment, the area of interest comprises a breast region of the patient, and the detector is configured to scan the breast region. In such a configuration, the ellipsoidal surface of the detector ideally forms a cavity, wherein the cavity has an opening configured to allow the patient's breast to be inserted at least partially in the cavity such that the ellipsoidal surface surrounds the breast of the patient. A positioning ring may further be disposed at the opening of the cavity to position the breast in the detector. In addition, an imaging couch may be configured to support the detector, wherein the couch is further configured for a patient to lie face down on the couch such that the patient's breast is imaged hanging freely and uncompressed inside the detector.

In another aspect of the invention, a method is disclosed for generating a PET image of an area of interest on a patient. The method comprises first introducing a positron-emitting radioisotrope into the area of interest, wherein the radioisotrope is configured to emit gamma rays when interacting with the area of interest. Then, a detector is placed in proximity of the area of interest, the detector having an ellipsoidal detection surface comprising a plurality of scintillation elements. The ellipsoid detection surface is configured such that a larger portion of gamma ray emissions strike normal or near normal to the detection surface than in rectangular or cylindrical detection surfaces. A signal is then generated in response to the gamma rays striking the scintillation elements.

Generally, introducing a positron-emitting radioisotrope comprises injecting a radiopharmaceutical comprising the positron emitting radioisotrope and a biologically active compound into the patient's body. Typically, the positron emitting radioisotrope comprises FDG.

In a preferred embodiment, the ellipsoidal surface comprises a scintillation element, and the signal is generated by transforming light from a gamma ray striking the scintillation element into a corresponding electric signal. The signal may then be analyzed to detect a coincidence event, the coincidence event comprising two gamma ray photons striking the detector surface within a specified time period. A line of coincidence of the gamma ray photons striking the detector may be determined, wherein the line of coincidence is correlated to the flight path of the gamma rays.

Where the detector surface is substantially spherical, the line of coincidence may be calculated by determining the location on the detector surface struck by the gamma ray and transforming the location from spherical coordinates to Cartesian coordinates. The signal may be further analyzed to determine a point of origin of the gamma ray along the line of coincidence. The point of origin may be derived by measuring the time of flight of the gamma rays, the attenuation of the gamma rays, or a combination of the two. An image of the area of interest may then be generated from the point of origin data.

For mammography scanning the patient may be positioned such that the patient's breast is surrounded by the ellipsoidal detection surface. Ideally, the patient's breast is imaged hanging freely and uncompressed inside the detector.

In another aspect of the invention, a method is disclosed for performing mammography by generating a PET image of a patient's breast. The method generally comprises introducing a positron-emitting radioisotrope into the patient, the radioisotrope configured to emit gamma rays when interacting with the area of interest, positioning at least a portion of the patient's breast into a detector having an ellipsoid detection surface, generating a signal in response to the gamma rays striking the detection surface, and imaging the patient's breast from the generated signal. The ellipsoid detection surface is configured such that a larger portion of gamma ray emissions strike normal or near normal to the detection surface than in rectangular or cylindrical detection surfaces.

Imaging the patient's breast generally comprises calculating a line of coincidence of the gamma ray photons striking the detector, wherein the line of coincidence is correlated to the flight path of the gamma rays, analyzing the signal to determine a point of origin of the gamma ray along the line of coincidence; and generating an image of the area of interest from the point of original data. The line of coincidence is preferably calculated by determining the location on the detector surface struck by the gamma ray and transforming the location from spherical coordinates to Cartesian coordinates. The point of origin may be found by measuring the time of flight or attenuation of the gamma rays.

In yet another aspect of the invention, a system for generating a PET image of an area of interest on a patient comprises a positron-emitting radioisotrope configured to emit gamma rays when interacting with the area of interest inside the patient's body, a detector having an ellipsoid detection surface, a processor configured to analyze a signal generated from the gamma rays striking the detection surface; and a display for generating an image of the breast, the image derived from of the processed signal.

Generally, the ellipsoidal detection surface comprises a scintillation element configured to generate light in response to gamma rays striking the ellipsoidal surface. The ellipsoidal surface is preferably substantially spherical, but may be spheroid.

The system may further comprise a positioning ring disposed at the opening of the cavity, the positioning ring adapted for positioning the breast in the detector. In addition, an imaging couch may be configured to support the detector, wherein the couch is further configured for a patient to lie face down on the couch such that the patient's breast is imaged hanging freely and uncompressed inside the detector.

In yet another aspect of the invention, a PET mammography scanner comprises a detector having a generally spheroid detection surface configured to surround the area of interest on a patient's breast, one or more scintillation elements coupled to the spheroid surface, the scintillation elements configured to generate light in response to gamma rays striking the ellipsoidal surface, means for generating a electrical signal from the illuminated scintillation element, and means for analyzing the generated electrical signal to generate an PET image of the patient's breast. The ellipsoid detection surface is configured such that a larger portion of gamma ray emissions strike normal or near normal to the detection surface than in rectangular or cylindrical detection surfaces. A means for positioning the breast in the detector and means for displaying the PET image may also be provided.

Further aspects of the invention will be brought out in the following portions of the specification, wherein the detailed description is for the purpose of fully disclosing preferred embodiments of the invention without placing limitations thereon.

DEFINITIONS

In the present specification and claims, reference will be made to phrases and terms of art which are expressly defined for use herein as follows:

As used herein, a gamma ray is an electromagnetic radiation emitted from radioactive substances.

As used herein, collimation is a filtering process of restricting the detection of photons emitted from a given area of interest into the detector system.

As used herein, a cyclotron is an accelerator that produces high-speed ions (e.g. protons and deuterons) under the influence of an alternating magnetic field, for bombardment and disruption of atomic nuclei in a target, and are used to produce clinically useful positron-emitting radionuclides.

As used herein, coincidence detection is the simultaneous detection of two 511 keV photons on opposite sides of a detector system. The annihilation event between a positron and an electron can be predicted to lie on a line joining the two points of photon detection.

As used herein, a positron is a subatomic particle of mass and charge equal to the electron but of opposite (i.e. positive) charge.

As used herein, a photon is a quantum of light or other electromagnetic radiation.

As used herein, a scintillator is a substance that emits visible light when hit by a subatomic particle or X or gamma rays.

As used herein, tomography is the recording of two-dimensional internal body images in a predetermined plane to allow an appreciation of the three-dimensional distribution of a property of bodily tissues.

As used herein, an ellipsoid is a three dimensional figure in which all planar cross sections are either ellipses or circles, and forming three semi-axes that can vary as to length.

As used herein, a spheroid is an ellipsoid having two of the three semi-axes being equal. A spheroid is oblate if the two equal semi-axes are larger than the third semi-axis. A spheroid is prolate if the two equal semi-axes are smaller than the third semi-axis.

As used herein, a sphere is a type of spheroid in which the generating ellipse is a circle.

DETAILED DESCRIPTION OF THE INVENTION

The PET detector of the present invention comprises a detection surface that is at least ellipsoidal, and preferably spheroid or substantially spherical. The Spherical PET Mammography Scanner (SPETMS) of the present invention is a scintillation camera for the detection of Gamma rays resulting from electron-positron annihilation reactions in vivo. Like conventional PET detectors imaging in three dimensions, it uses electronic rather than physical collimation which is accomplished by recording simultaneous 511 KeV Gamma rays traveling at 180° to each other.

Figure 2:
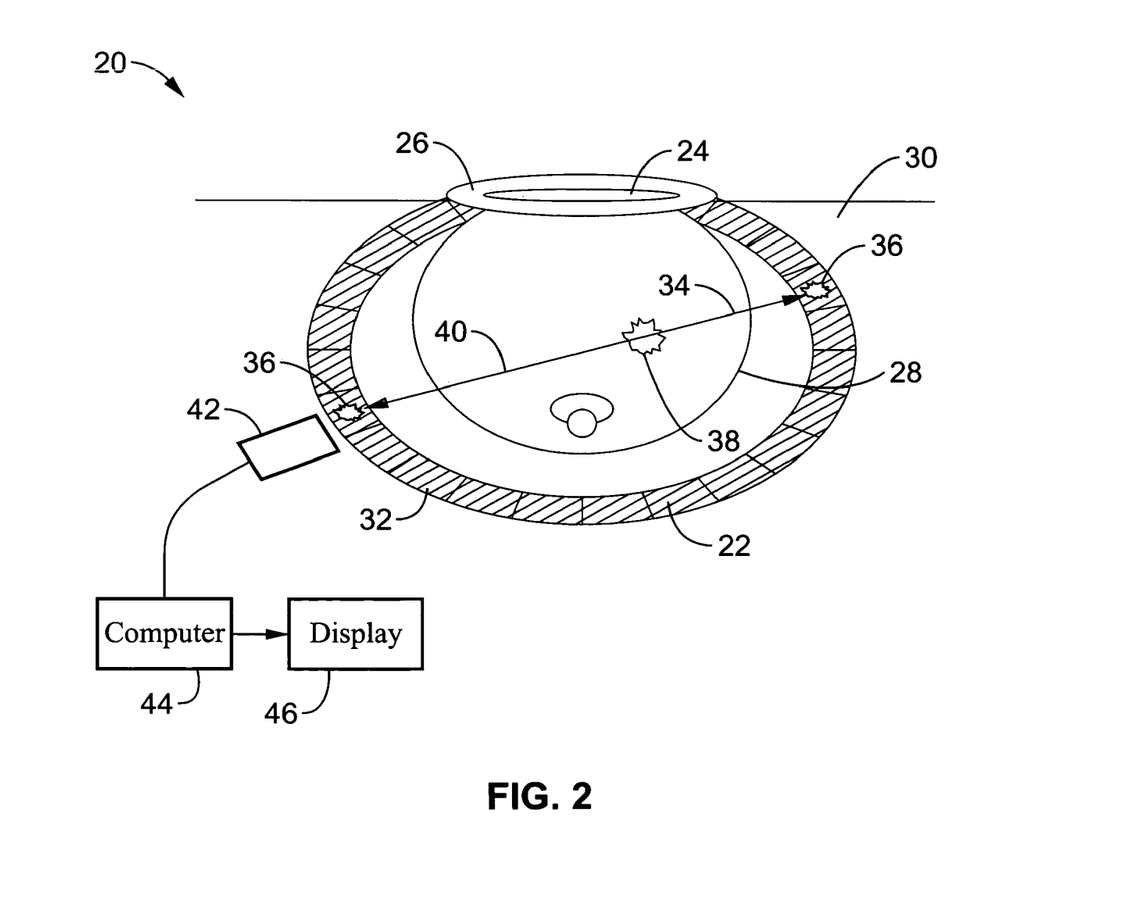
FIG. 2 is a side view of a detector having a spherical detection surface in accordance with the present invention surrounding the patient's breast.

FIG. 2 illustrates a detector 20 for breast imaging according to the present invention comprising a spherical surface 22. The detector 20 has an opening 24 and positioning ring 26 for insertion of the patient's breast 28. Preferably, the detector 20 is set into couch 30 such that the patient may lie face down on a couch 30 in the prone position with her pendant breast inside the detector 20. The breast 28 hangs freely and uncompressed inside the detector while positioning ring 26 orients the breast. Spherical surface 22 comprises a plurality of scintillator detector crystals 32 oriented on the spherical surface 22. Crystals 32 are inorganic crystals that emit visible light when hit by a gamma ray.

Scintillation crystals 32 generally comprise inorganic crystals that illuminate with interaction with gamma rays. One type of crystal that has been commonly used for PET scintillation material is bismuth germanium oxide (BGO). BGO crystals have good stopping power, i.e. they efficiently absorb the energy of the 511 keV gamma rays. However, BGO crystals have a fairly low light output, which directly impacts energy and spatial resolution. Lutetium oxyorthosilicate (LSO) crystals are relatively new crystals used in PET scanning, and have a much higher light output. LSO crystals also have a short light decay time, allowing a narrower coincidence window for reduced unrelated events. Both BGO and LSO crystals are non-hygroscopic (i.e. don't absorb water). Sodium iodide (NaI) crystals have a very high light output, but are hygroscopic and therefore must be hermetically sealed to prevent discoloration and reduced light output.

In PET, a positron-emitting radioisotrope is chemically incorporated into a biologically active compound, the combination of which is known as a radiopharmaceutical. Positrons are subatomic particles that resemble electrons, but carry a positive instead of negative charge. In preparation for a PET scan, a positron-labeled compound is administered. The radiopharmaceutical is introduced, usually through injection, into the patient's body, where it participates in specific physiological processes.

The radioisotopes used in PET are typically produced in cyclotrons. The most commonly used in clinical PET is fluorine-18 (18F), labeled to fluorodeoxyglucose to produce 18F-FDG, commonly referred to as FDG. This altered glucose molecule behaves sufficiently like normal glucose to participate in, and allow the imaging of, glucose metabolism. FDG is taken up preferentially by tissues that use glucose as their main energy source (e.g. malignant tumors and their metastases, myocardial cells, and neural tissue) making it particularly useful in clinical applications such as oncology, cardiology and neurology.

Other radioisotopes used in clinical PET include oxygen-15 (15O), N-13 (13N) and carbon-11 (11C). However, these isotopes have relatively short half-lives, i.e., the time taken for radioactive decay to reduce the amount of radioisotope to one-half the amount originally present. This short half-life limits these radioisotopes' utility in clinical studies, and requires the PET scanner to be co-located with the cyclotron that produces the radioisotope. The longer half-life of 18F, on the other hand, not only makes it significantly more practical in a clinical setting, but also means that it can be viably transported to sites away from the point of production.

The positrons emitted from the radiopharmaceutical travel a short distance in tissue before colliding with a local electron, e.g. positron decay 38 from a potential tumor location. When a positron collides with an electron, the particles are annihilated and transformed into two photons. The two photons travel out at a high energy level of 511 keV and at approximately 180° from each other forming a line of coincidence 40. When the photons interact with the crystals 32, a flash of visible light 36 is produced. The light is converted into an electrical signal by a photodetector 42, e.g. a photomultiplier tube, connected to the scintillator crystals 32. A number of photomultiplier tubes may be employed such that there is one photomultiplier tube 42 for every crystal 32, or alternatively, every 6×6 or 8×8 block of crystals. The electrical signal from the crystals are then amplified and analyzed by a computer 44 to process the information acquired by the PET scanner 20 to produce an image on a display device 46.

With the photons striking opposite sides of the detector 20, the technique known as coincidence detection is employed to map the tissue. Because the photons travel in opposite directions, the source of each pair of photons can be identified with great precision. The simultaneous emission of the photon and subsequent strike on the opposite sides of the detector 22 create a coincidence event that is registered if crystals 32 produce a signal within a very narrow time interval (in the nanosecond range.) The detection of a coincidence event localizes the positron annihilation 38 to a point lying somewhere on the line of coincidence 40 connecting the two detected crystals 32. During a scan, millions of coincidence events provide the information about the quantity and spatial location of the radioisotopes in the body.

Collimation, a filtering process discussed in detail below, is then performed to restrict the detection of photons emitted from a given area of interest into the detector system. Ideally, the only coincidence events recorded by a PET scanner are those that arise from a unique positron annihilation that occurs along the line between two activated detectors. These are referred to as "true coincidences", carrying useful information about the location of the positron emitter.

However, there are other types of coincidence events that degrade the image, including accidental, scatter and multiple coincidences. Because of physical and technical limitations, the exact timing of an event can be resolved down to only approximately 4 nanoseconds (ns). A timing window of 8–15 ns is thus typically used to define a coincidence. Accidental coincidences occur when two unrelated photons arising from separate positron decays occur during this finite time interval, and thus are detected and registered as a coincidence event. Since accidental events are produced by photons emitted from unrelated isotope decays, they do not carry any spatial information about the activity distribution. Scattered coincidences are those in which one or both of the annihilation photons are diverted from their original path before reaching the detector as a result of interactions within the body. Multiple coincidences occur when more than one positron annihilates during the finite coincidence time interval and carry ambiguous information about the positron location.

As only true coincidences contribute useful information to the image, and random and scattered coincidences contribute only 'noise', the fraction of random and scattered coincidences should be as small as possible. Therefore, the electronic signals from each coincidence event are analyzed by computer 44 to determine if they are "true" coincidental events. A mathematical reconstruction algorithm is then used to create an image of radioisotope tracer distribution in the breast. Because tumors take up FDG, malignant lesions in the breast will be seen as areas of high Gamma ray emissions. These mathematical models help to quantify metabolic activity and actual three-dimensional radioactive bio-distribution objectively, rather than via visual interpretation.

The spherical detection surface 22 provides a significant improvement over cylindrical or planar surfaces. SPETMS differs from other PET scanners used for either whole body imaging or mammography alone in that its detection surface will surround the area of interest (e.g., the breast) and that all Gamma rays traveling radially will strike normal to the surface of the detector and emissions resulting in chords will strike the detector surface at less oblique angles than they would in cylindrical or rectangular detectors. The following equations under Lambert's Law apply to a spherical detection surface:

$$A = \int_{-\frac{\pi}{2}}^{\frac{\pi}{2}} \int_0^{2\pi} R^2 \sin(\theta)\sin(\phi) d\theta d\phi$$

$\Psi = 4\pi R^2 \times$(number of photons emitted by the source)

For a 10 cm radius:

$A = (3.41)(\pi)(10^2) = 1071$ cm$^2$

For a source located at the center of the sphere 62, all gamma rays from true positron disintegrations will be traveling along radial lines and will strike the detector perpendicular and the maximum photon energy will be delivered to the detector. Ideally, if photon flux originating from the radioactive source is equal to $\Psi$, and each photon has energy hv, total energy detection would be:

$E_{tot} = 1071(hv)(\Psi$ photons)(kev)(cm$^2$)

For a rectangular detector having a length of 10 cm and a width of 7.5 cm:

$$E_{tot} = (8)(hv)(\Psi \text{ photons})(10\text{cm})(7.5\text{cm})$$
$$= 600(hv)(\Psi \text{ photons})(kev)(\text{cm}^2)$$

This feature will maximize the geometric efficiency of the detector by an advantage of (1071/600)=1.785. The increased efficiency results in better image contrast and resolution. Better resolution and contrast will improve sensitivity so that even very small malignancies not detectable on imaging devices now in use will be visible. In addition, since only cancer cells avidly take up and store FDG, benign masses will be readily distinguishable from malignant ones. This improvement in sensitivity and specificity will make it possible to detect malignant breast tumors much earlier in their natural history when they are more amenable to curative treatment while sparing women with benign masses the risks and morbidity of biopsy.

Figure 3:
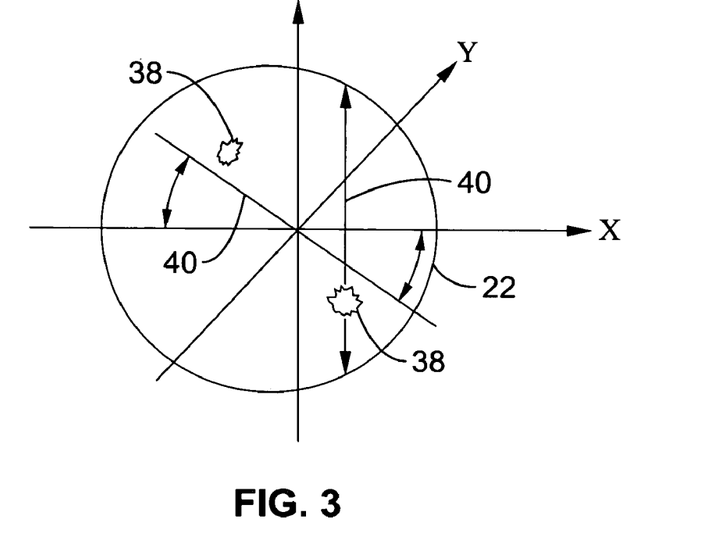
FIG. 3 is a schematic view of gamma rays striking the spherical surface.
Figure 4:
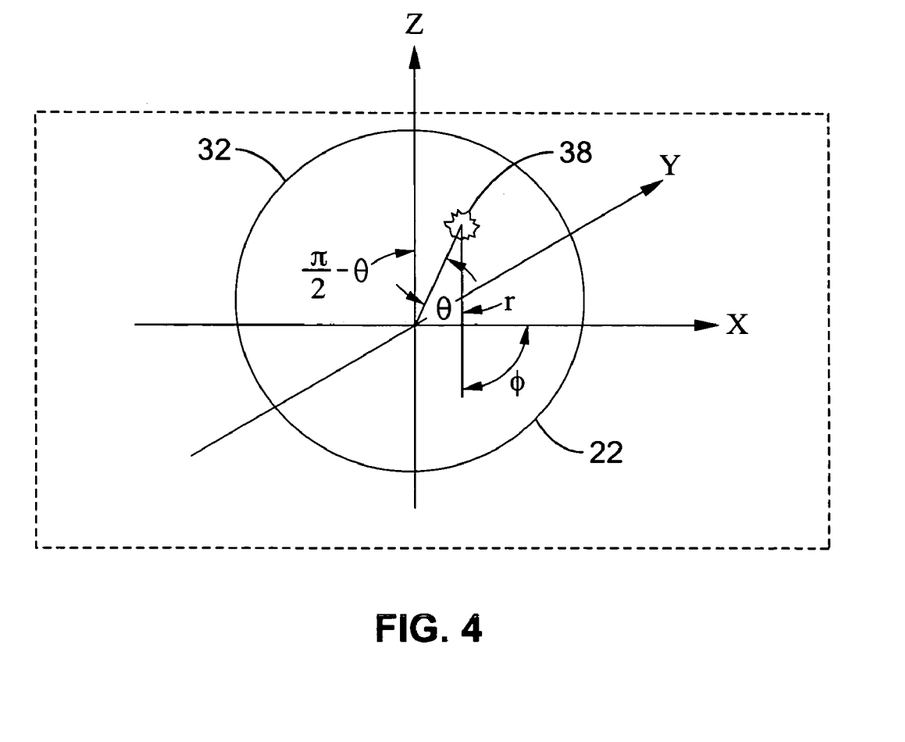
FIG. 4 illustrates an annihilation event as represented by spherical and Cartesian coordinates.

Now referring to FIGS. 3 and 4, the collimation for a spherical detector can be greatly facilitated by converting from Cartesian to spherical coordinates to determine a line of coincidence dimensional space along which the annihilation event occurred. As seen in FIG. 3, each event 38 results in two photons traveling in opposite directions such that each forms a line of coincidence 40 across the detector surface 22.

Referring to FIG. 4, each crystal 32 on the detector surface 22 will be assigned a location in spherical coordinates, θ and φ, in relation to the center of the sphere of radius, r. Values for θ range from −π/2 to π/2, and φ values range from 0 to 2π. When a γ-ray interaction is detected in a crystal 32 on the spherical detector 22, angles of θ and φ will automatically be assigned with respect to the center of the spherical detector.

The next step is to determine the detector coordinates in relation to the breast coordinates of the patient and transfer the recorded points to the breast coordinates, such that a precise three dimensional point localization of very small lesions in the uncompressed breast may be determined. The point of detection 38 on the surface of the sphere will be converted to a three dimensional point in spherical coordinates. Cartesian and spherical coordinates are related as follows:

$$X = r \sin(\theta)\cos(\phi)$$
$$Y = r \sin(\theta)\sin(\phi)$$
$$Z = r \cos(\theta)$$

A coincidental detection during the time window at a point on the sphere 22 that is at a 180° angle in spherical coordinates to the first detection event will, as in conventional PET, determine a line of coincidence 40.

The set of coordinates corresponding to a point on the spherical detector surface 22 that define the line of coincidence 40 can be calculated as follows.

$$X' = r(-\sin(\theta-\pi/2)\cos(\phi+2\pi))$$
$$Y' = r(-\sin(\theta-\pi/2)\sin(\phi+2\pi))$$
$$Z' = r(-\cos(\theta-\pi/2))$$

Because the radius of the sphere, r, is known, and the angles θ and φ have been recorded, the points where the two γ-rays were emitted as a result of the positron/electron interaction and the locations where they strike the spherical detector can be calculated as follows.

$$X = r(\sin(\theta)*\cos(\phi)) \quad X' = r(-\sin(\theta-\pi/2)(\cos(\phi+2\pi)))$$
$$Y = r(\sin(\theta)*\sin(\phi)) \quad Y' = r(\sin(\theta-\pi/2)\sin((\phi+2\pi)))$$
$$Z = r(\cos(\theta)) \quad Z' = r(\cos(\theta-\pi/2))$$

Where:

$$X+X'=0$$
$$Y+Y'=0$$
$$Z+Z'=0$$

For example, for a sphere having a radius, r=15 cm, and an event is recorded at the angles θ=π/4 and φ=3π/2, the three dimensional coordinates of the γ ray interaction with the detector will be:

$$X = 15(\sin(\pi/4)(\cos(\pi/3)) = 5.3 \text{ cm}$$
$$Y = 15(\sin(\pi/4)(\sin(\pi/3)) = 9.18 \text{ cm}$$
$$Z = 15(\cos(\pi/4)) = 10.61 \text{ cm}$$

and $$X' = 15(-\sin(\pi/4-\pi/2)(\cos(\pi/3+2\pi)) = 5.3$$
$$Y' = 15(-\sin(\pi/4-\pi/2)(\sin(\pi/3+2\pi)) = 9.18$$
$$Z' = 15(-\cos(\pi/4-\pi/2)) = -10.61$$

If a simultaneous event is recorded at the following coordinates on the sphere we can consider the line between the two points to be a line of coincidence.

Once the line of coincidence 40 is determined, the signal can be further evaluated to find where on the line of coincidence the event occurred. One method to determine the point of origin 38 along the line of coincidence 40 is by measuring the differences in time of arrival of the gamma rays 40 at the detector crystals. While it may be difficult to measure time of flight differences given the small differences involved and the rapidity of the speed of light, improved detection capability and increases in computing power could make the method increasingly accurate.

Differences in attenuation of the detected coincident γ-rays may also be used to localize the tumor. Since breast tissue is very homogenous, high energy photons will lose energy at a fairly constant rate as they travel through the breast. Therefore, the recorded photon detection with the higher energy will have traveled through less tissue, and can be considered closer to the location of the radioactive decay event on the line of coincidence. Counts may then be weighted on the basis of photon energy as well as number. As a result, instead of lines of coincidence where there is an equal probability of a decay event at any point along its length, the above method will result in lines of coincidence more likely to form a point image at the location of FDG uptake and positron emission 30.

Another approach may be to use both the attenuation and time of flight methods together to accurately locate the tumor in the breast. If the attenuation observed is consistent with the time of flight, the result will not only more accurately locate the lesion, but also improve confidence that a true event has been detected. Because of the high geometric efficiency of the spheroid detector, adequate counts may be obtained even if the counts are limited to only those consistent with each other in both time of flight and attenuation methods.

Figure 5:
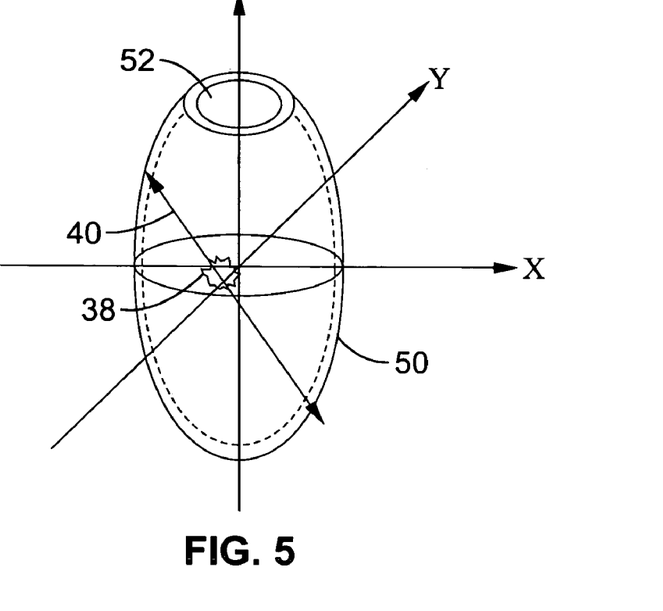
FIG. 5 illustrates schematic view of a prolate spheroid detector surface in accordance with the present invention.

In an alternative embodiment shown in FIG. 5, ellipsoid shapes other than true spherical surfaces may be used for the detector surface. For example, the detector surface may be spheroid, or in particular, a prolate spheroid surface 50, having an opening 52 situated at the top of the major axis. While less efficient than a spherical surface, an elongated spheroid may present less manufacturing difficulties, yet still offering superior geometry to other types of detectors, since a larger portion of the gamma rays 40 will be normal to the detector surface 50 than in a cylindrical or rectangular design.

Figure 6:
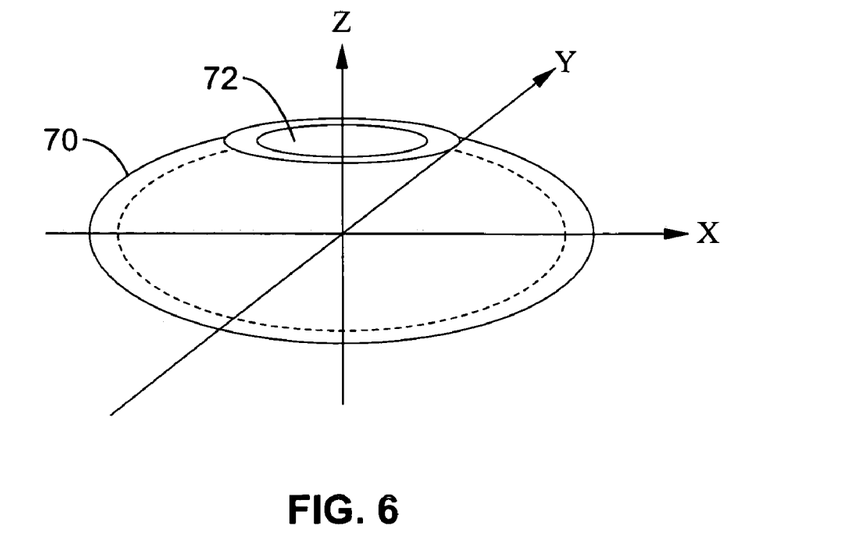
FIG. 6 illustrates schematic view of an oblate spheroid detector surface in accordance with the present invention.

One effect of the spherical detector surface is that the device has optimal sensitivity when the source is at the center of the sphere. To maintain optimal efficiency, we would need to know the location of the lesion to properly place the patient in the optimal position in the scanner. However, the location of the lesion is what we are trying to find with the PET scanner. FIG. 6 illustrates an embodiment having a detector surface 70 comprising an oblate spheroid or ellipsoid that is larger in the X and/or Y axes than the Z axis. The detector has an enlarged opening 72 so that the patient's breast may be passed through the detector with periodic scans taken. The ability to re-position the patient in the Z axis might be needed as well so that suspicious areas could be placed at the center of the sphere.

Construction of the device will typically comprise the following steps:

1. Using a large block of LSO or BGO, construct the crystal surface;
2. Attach Photomultipliers to crystal;
3. Build electronic circuitry for measuring coincidence, energy, and location of interactions on the sphere;
4. Fit to couch in which the patient can lie in the prone position with the pendant breast positioned in the spherical detector.

Figure 7:
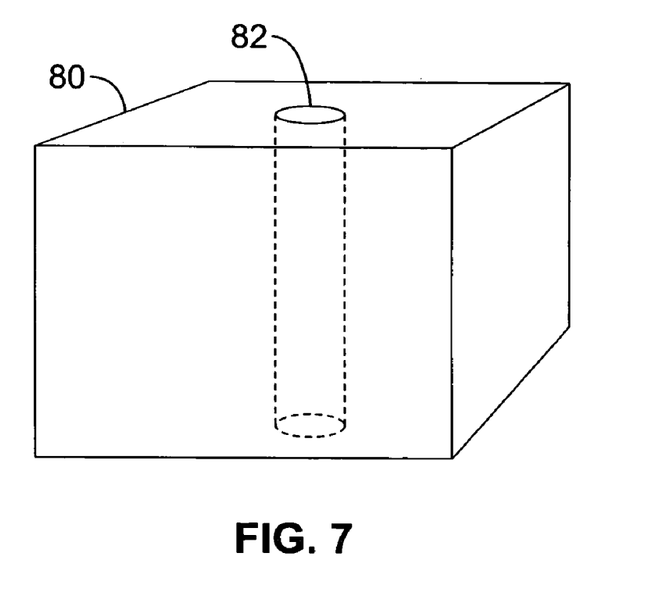
FIGS. 7–9 illustrate steps for fabricating a detector out of a block of crystal.

FIGS. 7–10 illustrate the construction of the detector surface. It will be appreciated that breast size and shape differ significantly between individual women. To accommodate as many women as possible while still keeping the detector on a manageable scale, the radius of the spherical surface may preferably range between 10 cm and 15 cm, and optimally at about 12 cm. For a 24 cm diameter sphere, 27×27×27 cm³ BGO crystal block 80 is used to obtain a minimum crystal thickness of 3 cm for the detector. A 3 cm×24 cm cylinder 82 is then drilled into one side, as illustrated in FIG. 7.

Figure 8:
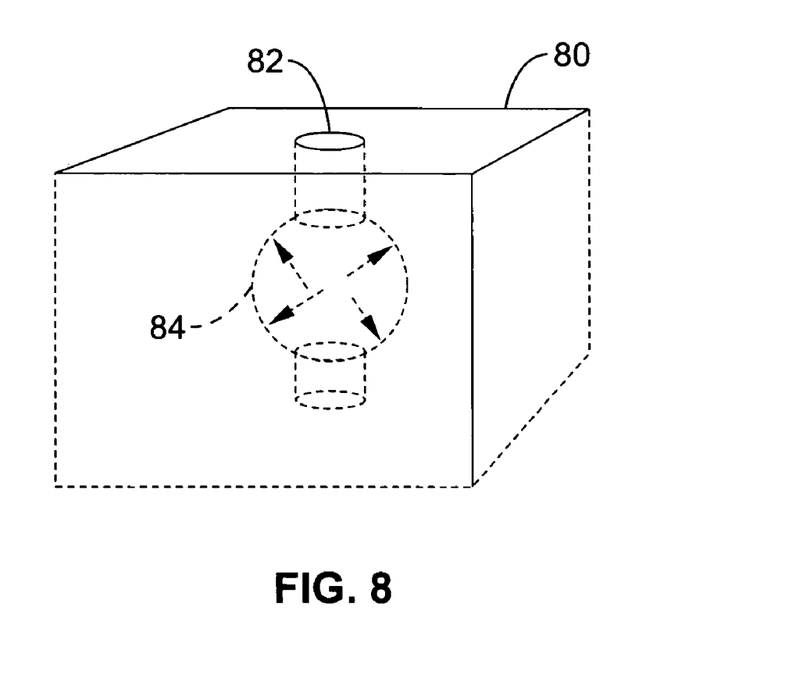
Figure 9:
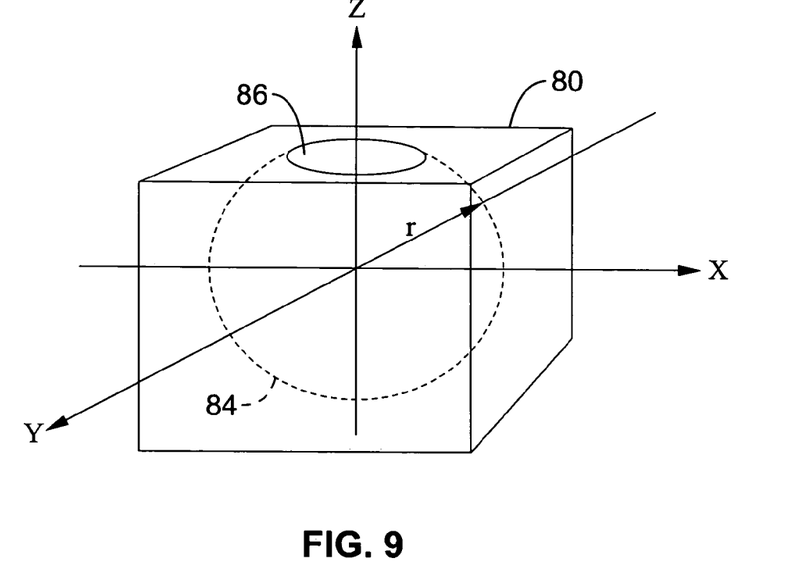
Figure 10:
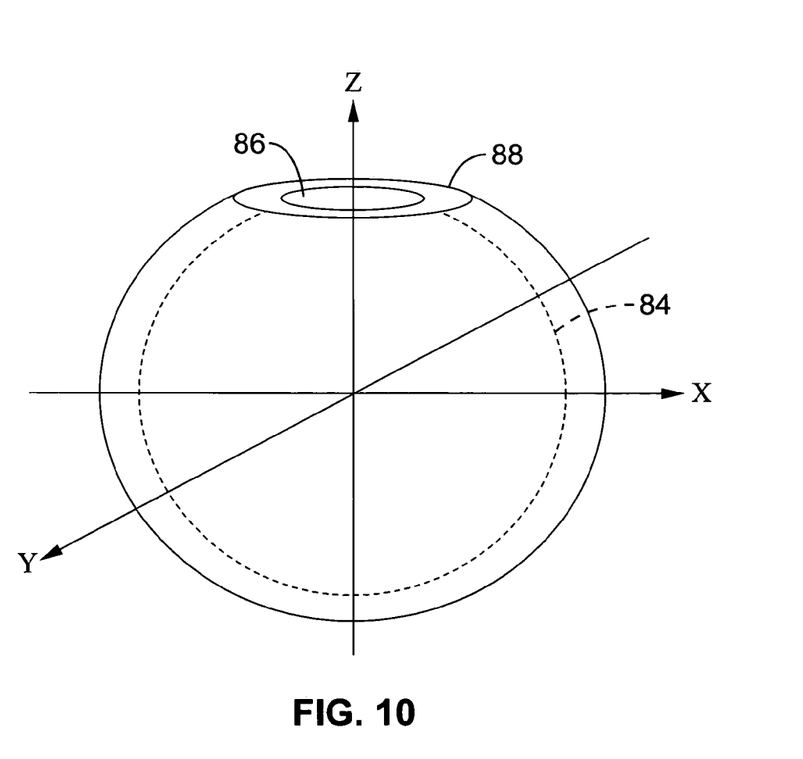
FIG. 10 illustrates a fabricated spherical detector with a positioning ring in accordance with the present invention.

Now referring to FIG. 8, the next step will be to start at the point that will be the center of the sphere and begin to carve out a sphere 84 with the desired radius of curvature. In an exemplary embodiment, when hollowing out of the block is completed, we will have sphere 84 of radius 12 cm inside of the block, as shown in FIG. 9. The top of block 80 is then bored to form top opening 86. Finally, the corners of the block are shaved down to form a sphere with radius 12 cm, wall thickness of 3 cm and an opening at the top 12 cm in diameter, as shown in FIG. 10.

As can be seen, therefore, the present invention provides for mammography using a detector shape heretofore unknown. It will be appreciated that, while the above discussion is directed to mammography, the invention could be used for imaging other parts of the body, and even the entire body. Although the description above contains many details, these should not be construed as limiting the scope of the invention but as merely providing illustrations of some of the presently preferred embodiments of this invention. Therefore, it will be appreciated that the scope of the present invention fully encompasses other embodiments which may become obvious to those skilled in the art, and that the scope of the present invention is accordingly to be limited by nothing other than the appended claims, in which reference to an element in the singular is not intended to mean "one and only one" unless explicitly so stated, but rather "one or more." All structural, chemical, and functional equivalents to the elements of the above-described preferred embodiment that are known to those of ordinary skill in the art are expressly incorporated herein by reference and are intended to be encompassed by the present claims. Moreover, it is not necessary for a device or method to address each and every problem sought to be solved by the present invention, for it to be encompassed by the present claims. Furthermore, no element, component, or method step in the present disclosure is intended to be dedicated to the public regardless of whether the element, component, or method step is explicitly recited in the claims. No claim element herein is to be construed under the provisions of 35 U.S.C. 112, sixth paragraph, unless the element is expressly recited using the phrase "means for."

What is claimed is:

1. A method for generating a PET image of an area of interest on a patient, the method comprising:
   introducing a positron-emitting radioisotope into the area of interest, the radioisotope configured to emit gamma rays when interacting with the area of interest;
   placing a detector in proximity of the area of interest;
   wherein the detector has a spherical detection surface;
   wherein the spherical detection surface is configured such that a larger portion of gamma ray emissions strike normal or near normal to the detection surface than in rectangular or cylindrical detection surfaces;
   generating a signal in response to a gamma ray striking the spherical detection surface;
   analyzing the signal to detect a coincidence event;
   said coincidence event comprising two gamma ray photons striking the detection surface within a specified time period;
   calculating a line of coincidence of the gamma ray photons striking the spherical detection surface; and imaging the area of interest from the generated signal;
   wherein the line of coincidence is correlated to the flight path of the gamma rays;
   wherein calculating the line of coincidence comprises determining the locations on the detector surface struck by the gamma rays and transforming the locations from spherical coordinates to Cartesian coordinates.

2. A method as recited in claim 1, wherein introducing a positron-emitting radioisotope comprises injecting a radiopharmaceutical comprising the positron emitting radioisotope and a biologically active compound into the patient's body.

3. A method as recited in claim 2, wherein the positron emitting radioisotope comprises FDG.

4. A method as recited in claim 1, wherein the spherical detection surface comprises a scintillation element, and wherein generating a signal comprises transforming light generated from a gamma ray striking the scintillation element into a corresponding electric signal.

5. A method as recited in claim 1, further comprising analyzing the signal to determine a point of origin of the gamma ray along the line of coincidence.

6. A method as recited in claim 5, wherein determining a point of origin comprises measuring the time of flight of the gamma ray.

7. A method as recited in claim 5, wherein determining a point of origin comprises measuring the attenuation of the gamma ray.

8. A method as recited in claim 5, further comprising generating an image of the area of interest from the point of origin data.

9. A method as recited in claim 1, wherein placing a detector in proximity of the area of interest comprises positioning the patient such that the patient's breast is surrounded by the spherical detection surface.

10. A method as recited in claim 9, further comprising generating an image of the patient's breast hanging freely and uncompressed inside the detector.

11. A method for performing mammography by generating a PET image of a patient's breast, the method comprising:
   introducing a positron-emitting radioisotrope into the patient, the radioisotrope configured to emit gamma rays when interacting with the area of interest;
   positioning at least a portion of the patient's breast into a detector, the detector having a spherical detection surface;
   wherein the spherical detection surface is configured such that gamma ray emissions strike normal or near normal to the spherical detection surface;
   generating a signal in response to the gamma rays striking the detection surface;
   imaging the patient's breast from the generated signal
   wherein imaging the patient's breast comprises:
   calculating a line of coincidence of the gamma ray photons striking the detection surface, wherein the line of coincidence is correlated to the flight path of the gamma rays;
   wherein calculating the line of coincidence comprises determining the locations on the detection surface struck by the gamma ray and transforming the locations from spherical coordinates to Cartesian coordinates;
   analyzing the signal to determine a point of origin of the gamma ray along the line of coincidence; and
   generating an image of the area of interest from the point of original data.

12. A method as recited in claim 11, wherein the spherical detection surface comprises a scintillation element, and wherein generating a signal comprises transforming light generated from a gamma ray striking the scintillation element into a corresponding electric signal.

13. A method as recited in claim 11, wherein determining a point of origin comprises measuring the time of flight of the gamma ray.

14. A method as recited in claim 11, wherein determining a point of origin comprises measuring the attenuation of the gamma ray.

15. A method as recited in claim 11, wherein positioning the patient's breast inside the detector comprises surrounding the patient's breast by the spherical detection surface.

16. A method as recited in claim 15, wherein the patient's breast hangs freely and uncompressed inside the detector.

17. A system for generating a PET image of an area of interest on a patient, the system comprising:
   a positron-emitting radioisotrope, the radioisotrope configured to emit gamma rays when interacting with the area of interest inside the patient's body;
   a detector having a spherical detection surface;
   wherein the spherical detection surface is configured such that gamma ray emissions strike normal or near normal to the detection surface without physical collimation of gamma ray emissions;
   and
   a processor configured to analyze a signal generated by a coincidence event comprising two gamma ray photons striking the detection surface within a specified time period;
   wherein the processor is further configured to calculate a line of coincidence of the gamma ray photons striking the spherical detection surface by determining the locations on the detector surface struck by the gamma rays and transforming the locations from spherical coordinates to Cartesian coordinates.

18. A system as recited in claim 17, wherein the spherical detection surface comprises a scintillation element configured to generate light in response to gamma rays striking the ellipsoidal surface.

19. A system as recited in claim 18, wherein the scintillation element comprises an array of scintillation crystals.

20. A system as recited in claim 18, further comprising at least one photomultiplier coupled to the scintillation element;
   said photomultiplier configured to convert the light emitted from the scintillation element into electronic signals.

21. A system as recited in claim 20, wherein the processor analyzes the signal to determine the location of the gamma ray origin.

22. A system as recited in claim 18, wherein the scintillation element comprises a crystal made of BGO.

23. A system as recited in claim 18, wherein the scintillation element comprises a crystal made of LSO.

24. A system as recited in claim 17, wherein the area of interest comprises a breast region of the patient, and wherein the detector is configured to scan the breast region.

25. A system as recited in claim 24, wherein the spherical surface of the detector forms a cavity;
   said cavity having an opening configured to allow the patient's breast to be inserted at least partially in the cavity such that the spherical surface surrounds the breast of the patient.

26. A system as recited in claim 25, further comprising a positioning ring disposed at the opening of the cavity;
   said positioning ring adapted for positioning the breast in the detector.

27. A system as recited in claim 26, further comprising an imaging couch configured to support the detector;
   wherein the couch is further configured for a patient to lie face down on the couch such that the patient's breast is imaged hanging freely and uncompressed inside the detector.

28. As system as recited in claim 17, wherein the positron emitting radioisotrope comprises FDG.

* * * * *